United States Patent [19]

Rao

[11] Patent Number: 4,782,167

[45] Date of Patent: Nov. 1, 1988

[54] PROCESS FOR PREPARING BUTYROLACTONES AND BUTANEDIOLS

[75] Inventor: Velliyur N. M. Rao, Wilmington, Del.

[73] Assignee: E. I. Du Pont de Nemours and Company, Wilmington, Del.

[21] Appl. No.: 6,239

[22] Filed: Jan. 23, 1987

[51] Int. Cl.$^4$ .................... C07D 307/32; C07C 29/136
[52] U.S. Cl. .................... 549/326; 549/325; 568/864
[58] Field of Search .................... 549/326, 325, 864; 568/864

[56] References Cited

U.S. PATENT DOCUMENTS

| | | | |
|---|---|---|---|
| 4,096,156 | 6/1978 | Freudenberger et al. | 549/326 |
| 4,105,674 | 8/1978 | De Thomas et al. | 549/326 |
| 4,550,185 | 10/1985 | Mabry et al. | 549/508 |
| 4,609,636 | 9/1986 | Mabry et al. | 502/183 |

FOREIGN PATENT DOCUMENTS

| | | | |
|---|---|---|---|
| 2133768 | 1/1972 | Fed. Rep. of Germany | 549/325 |
| 1149784 | 4/1969 | United Kingdom | 549/325 |

OTHER PUBLICATIONS

Abstract of JA-7300823-R (Jan. 1973).
Abstract of J6 1115-079-A (Jun. 1986).

*Primary Examiner*—Norma S. Milestone

[57] ABSTRACT

A process is disclosed for preparing butyrolactones, butanediols, and mixtures thereof comprising hydrogenating a hydrogenatable precursor in the presence of an aqueous reaction medium and a catalyst comprising palladium or combinations thereof with rhenium and at least one support selected from the oxides of titanium, zirconium, and hafnium.

10 Claims, No Drawings

PROCESS FOR PREPARING BUTYROLACTONES AND BUTANEDIOLS

FIELD OF THE INVENTION

The invention concerns making butyrolactones, butanediols, and mixtures thereof by hydrogenating a variety of hydrogenatable precursors such as maleic acid, fumaric acid, succinic acid, itaconic acid, or mixtures thereof.

BACKGROUND OF THE INVENTION

Butyrolactone is a known compound which is employed in the synthesis of pyrrolidone, glutaric acid, and many other compounds. Improved processes for preparing butyrolactone are of interest to the chemical industry.

The following references disclose known processes for making butyrolactone. U.S. Pat. No. 4,096,156 discloses a process for the preparation of gamma-butyrolactone by catalytic hydrogenation of maleic acid, maleic acid anhydride, succinic acid, succinic acid anhydride, or fumaric acid, or of a mixture of two or more of these compounds. The catalyst contains a mixture of an element of the VIII$^{th}$ subgroup of the periodic system of elements or of one of its compounds with an element of group IB of the periodic system of elements or of one of its compounds.

U.S. Pat. No. 4,105,674 discloses a process for producing gamma-butyrolactone by hydrogenating a feed compound selected from the group consisting of maleic acid, succinic acid, maleic anhydride, succinic anhydride, and mixtures of any of the foregoing in the vapor phase. The reaction is conducted in the presence of a Cu-Pd or Cu-Pt catalyst.

SUMMARY OF THE INVENTION

The present invention provides a process for preparing butyrolactones, butanediols, and mixtures thereof comprising hydrogenating a hydrogenatable precursor in the presence of an aqueous reaction medium and a catalyst comprising palladium or combinations thereof with rhenium and at least one support selected from the oxides of titanium, zirconium, and hafnium.

DETAILED DESCRIPTION OF THE INVENTION

The invention a process for making butyrolactones, butanediols, and mixtures thereof by hydrogenating a wide variety of hydrogenatable precursors such as maleic acid, maleic anhydride, succinic acid, succinic acid anhydride, fumaric acid, malic acid, dimethyl succinate, butyrolactones, itaconic acid or mixtures thereof. These precursors can be described as dicarboxylic acids, dicarboxylic acid esters, lactones, or mixtures of said acids, esters, lactones and/or anhydrides. Preferably, the hydrogenatable precursor is an acid and, most preferably, succinic acid, itaconic acid, maleic acid, or fumaric acid. The methods of the invention are characterized in that they can be oriented, as desired, toward high ratios of butyrolactones to butanediols or vice versa.

The catalyst of this invention comprises palladium or combinations thereof with rhenium and at least one support selected from the oxides of titanium, zirconium, and hafnium. Preferably, the catalyst comprises a combination of palladium and rhenium and the support is titanium oxide, and most preferably, the catalyst comprises from about 1 to about 19 weight percent palladium and from about 4 to about 76 weight percent rhenium. The catalyst provides substantially 100% conversion of the precursor, high selectivity to and yield of product, and the advantage of being able to control the product ratio of butyrolactone/butanediol by varying the reaction temperature, hydrogen pressure and flow rate of the aqueous reaction medium.

Preferably, the process is conducted at a temperature of from about 100° C. to about 250° C., and most preferably from about 125° C. to about 225° C. Preferably, the process is conducted at a pressure of from about 3.5 MPa (500 psig) to about 27.6 MPa (4000 psig), and most preferably from about 3.5 MPa (500 psig) to about 17.3 MPa (2500 psig).

The process is conducted in the presence of an aqueous reaction medium which can be water or an aqueous solution containing water soluble substances such as methanol, ethanol, tetrahydrofuran or 1,4-dioxane. Preferably, the aqueous reaction medium is water. The concentration of precursor is not critical. The precursor can be employed in dilute solutions to near the maximum solubility level, typically from about 1 to about 50 weight percent.

The liquid phase hydrogenation of the invention can be run using conventional apparatus and techniques in a stirred-tank reactor or in a fixed-bed reactor. Hydrogen is fed continuously, generally in considerable stoichiometric excess with no inert diluent gases. Unreacted hydrogen can be returned to the reactor as a recycle stream. The reaction can be run in the batch or continuous mode.

The invention is further described in the following examples wherein all parts and percentages are by weight and degrees are Celsius. Catalysts used in the Examples and Comparative Experiment were prepared according to the following general precedure.

EXAMPLES

Catalyst Preparation

The catalysts were prepared by adding 20 g of support to a solution containing the desired amount of PdCl$_2$, 3 mL of concentrated hydrochloric acid and 15 mL of distilled water. The resultant slurry was stirred for three hours at ambient temperature and dried at 110° for 18 hours. The resulting supported catalyst was then heated in a furnace for one hour at 150° in an atmosphere of helium (flow rate 100 mL/min), followed by heating at 150° for one hour and 300° for three hours in an atmosphere of helium (flow rate 100 mL/min) and hydrogen (flow rate 100 mL/min). While still maintaining the hydrogen helium atmosphere, the catalyst was cooled to ambient temperature and passivated at ambient temperature with an atmosphere of 1.8% oxygen in nitrogen for 18 hours.

The resulting reduced catalyst was added to a solution containing the desired amount of ammonium perrhenate and 6 mL of distilled water. The resultant slurry was treated as described above.

The catalyst so prepared were granulated to 16 to 19 mesh (U.S. Standard Sieve Units) and charged into the reactor employed in the Examples and Comparative Experiments. Prior to start of the liquid feed the granulated catalysts were reduced in the reactor for about two hours each at 100°, 150°, and 200° in a stream of hydrogen.

EXAMPLES 1-4

Succinic Acid Hydrogenation

A solution of 5% succinic acid and 2% dioxane in water was passed through a fixed bed of 4.12 g of 1% Pd/4% Re on titanium oxide catalyst contained in a glass lined stainless steel reactor (empty reactor volume 6 mL) at the designated liquid flow rate along with hydrogen at a flow rate of 50 mL/minute. The temperature of the reactor was maintained at the desired temperature using a fluidized, barricaded sand bath. Reaction pressure was controlled by means of a back pressure regulator. Product leaving the reactor was analyzed by conventional chromatography to determine selectivity to tetrahydrofuran (THF), 1,4-butanediol (BDO) and gamma-butyrolactone (GBL). Temperature, pressure and liquid feed rate were varied to determine conversion, product split and selectivity. The results are shown in Table 1.

TABLE 1
Succinic Acid Hydrogenation

| Exp. | Temp (°) | Press. MPa (psig) | Flow (mL/hr) | THF (%) | GBL (%) | BDO (%) | Conv |
|---|---|---|---|---|---|---|---|
| 1 | 200 | 3.5 (500) | 22.4 | 1.74 | 90.32 | 7.94 | 100.00 |
| 2 | 200 | 6.9 (1000) | 5.6 | 8.58 | 5.00 | 86.42 | 98.69 |
| 3 | 150 | 3.5 (500) | 5.6 | 0.00 | 89.66 | 10.34 | 100.00 |
| 4 | 150 | 6.9 (1000) | 11.2 | 0.00 | 90.23 | 9.77 | 97.70 |

COMPARATIVE EXPERIMENTS A-B

Succinic Acid Hydrogenation

The process described in Example 1 was substantially repeated two times except that the reaction mixture was a solution of 5% succinic acid and 2% dioxane in water and the catalyst was 1.70 g of 1% Pd and 4% Re on carbon. The results are shown in Table 2.

TABLE 2
Succinic Acid Hydrogenation

| Exp. | Temp (°) | Press. MPa (psig) | Flow (mL/hr) | THF (%) | GBL (%) | BDO (%) | Conv |
|---|---|---|---|---|---|---|---|
| A | 200 | 6.9 (1000) | 5.4 | 81.16 | 1.23 | 17.60 | 89.31 |
| B | 200 | 6.9 (1000) | 11.2 | 51.23 | 21.66 | 27.11 | 95.56 |

EXAMPLES 5-7

Itaconic Acid Hydrogenation

The process described in Example 1 was substantially repeated three times except that the reaction mixture was a solution of 4% itaconic acid and 2% dioxane in water and the catalyst was 4.12 g of 1% Pd and 4 % Re on titanium oxide. Product leaving the reactor was analyzed by conventional chromatography to determine selectivity to 3- and 4- methyl gamma-butyrolactone (MeGBL(3&4)) and 2-methyl-1,4-butanediol (MeBDO). The results are shown in Table 3.

TABLE 3
Itaconic Acid Hydrogenation

| Exp. | Temp (°) | Press MPa (psig) | Flow (ml/hr) | MeGBL (3 & 4) (%) | MeBDO (%) | Conv |
|---|---|---|---|---|---|---|
| 5 | 200 | 3.5 (500) | 12 | 98.58 | 1.42 | 81.08 |
| 6 | 175 | 3.5 (500) | 6 | 98.16 | 3.84 | 99.61 |
| 7 | 150 | 3.5 (500) | 3 | 95.69 | 4.31 | 84.06 |

EXAMPLES 8-11

Maleic Acid Hydrogenation

The process described in Example 1 was substantially repeated four times except that the reaction mixture was a solution of 5% maleic acid and 2% dioxane in water, the pressure was 3.5 MPa (500 psig), and the catalysts were as specified in Table 4. In Examples 8 and 9, the catalysts were 1% Pd and 4% Re; in Example 10, the catalyst was 0.5% Pd and 0.5% Re; and in Example 11, the catalyst was 0.5% Pd. The results are shown in Table 4.

TABLE 4
Maleic Acid Hydrogenation

| Exp | Temp (°) | Flow (ml/hr) | Catalyst | Support | THF (%) | GBL (%) | BDO (%) | Conv |
|---|---|---|---|---|---|---|---|---|
| 8 | 175 | 12.0 | Pd/Re | Zr Oxide | 1.04 | 88.87 | 10.09 | 83.1 |
| 9 | 200 | 18.0 | Pd/Re | Zr Oxide | 1.47 | 92.22 | 6.31 | 92.1 |
| 10 | 200 | 33.6 | Pd/Re | Ti Oxide | 0.49 | 98.45 | 1.06 | 88.1 |
| 11 | 200 | 11.2 | Pd | Ti Oxide | 0 | 98.77 | 0 | 45.6 |

What is claimed is:

1. A process for preparing butyrolactones, butanediols, and mixtures thereof comprising hydrogenating a hydrogenatable precursor in the presence of an aqueous reaction medium and either (1) a catalyst consisting essentially of palladium and at least one support selected from the oxides of titanium, zirconium, and hafnium or (2) a catalyst comprising a combination of palladium and rhenium and at least one support selected from the oxides of titanium, zirconium and hafnium.

2. A process according to claim 1, wherein the hydrogenatable precursor is an acid.

3. A process according to claim 2, wherein the hydrogenatable precursor is selected from the group consisting of succinic acid, itaconic acid, maleic acid, or fumaric acid.

4. A process according to claim 2, wherein the catalyst comprises a combination of palladium and rhenium and the support is titanium oxide.

5. A process according to claim 4, wherein the catalyst comprises from about 1 to about 19 weight percent palladium and from about 4 to about 76 weight percent rhenium.

6. A process according to claim 5, wherein the process is conducted at a temperature of from about 100° C. to about 250° C.

7. A process according to claim 6, wherein the process is conducted at a temperature of from about 125° C. to about 225° C.

8. A process according to claim 5, wherein the process is conducted at a pressure of from about 3.5 MPa to about 27.6 MPa.

9. A process according to claim 8, wherein the process is conducted at a pressure of from about 3.5 MPa to about 17.3 MPa.

10. A process according to claim 8, wherein the aqueous reaction medium is water.

* * * * *